United States Patent [19]

Fengler et al.

[11] Patent Number: 4,468,392
[45] Date of Patent: Aug. 28, 1984

[54] SULPHINYL- AND SULPHONYL-AZACYCLOHEPTAN-2-ONES, AND THEIR USE AS FEED ADDITIVES

[75] Inventors: Gerd Fengler; Artur Botta, both of Krefeld; Martin Scheer; Friedrich Berschauer, Wuppertal, all of Fed. Rep. of Germany

[73] Assignee: Bayer Aktiengesellschaft, Leverkusen, Fed. Rep. of Germany

[21] Appl. No.: 488,948

[22] Filed: Apr. 28, 1983

[30] Foreign Application Priority Data

May 8, 1982 [DE] Fed. Rep. of Germany ....... 3217373

[51] Int. Cl.³ .................. A61K 31/55; C07D 223/10; C07D 401/12; C07D 417/12
[52] U.S. Cl. .................. 424/244; 424/263; 424/270; 260/239.3 R
[58] Field of Search .................. 260/239.3 R; 424/244

[56] References Cited

PUBLICATIONS

Noller, "Chemistry of Organic Compounds, " 2nd Ed. pp. 278–279, 285, (Saunders) (1957).

Primary Examiner—Robert T. Bond
Attorney, Agent, or Firm—Sprung Horn Kramer & Woods

[57] ABSTRACT

The invention relates to sulphinyl- and sulphonyl-azacycloheptan-2-ones defined infra in Formula (I), processes for their preparation and their use as agents for promoting growth, and improving the fat to lean ratio utilization in animals.

11 Claims, No Drawings

SULPHINYL- AND SULPHONYL-AZACYCLOHEPTAN-2-ONES, AND THEIR USE AS FEED ADDITIVES

The invention relates to new sulphinyl- and sulphonyl-azacycloheptan-2-ones, processes for their preparation and their use as agents for promoting growth, improving fat to lean meat ratio and feed utilization in animals.

It has been found that the new sulphinyl- and sulphonyl-azacycloheptan-2-ones of the formula (I)

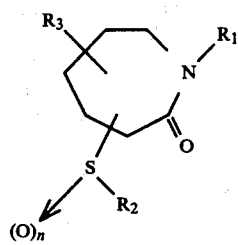

in which
n denotes 1 or 2,
$R^1$ represents H, optionally substituted alkyl, optionally substituted aryl, optionally substituted acyl and alkylcarbamoyl,
$R^2$ denotes optionally substituted alkyl, optionally substituted alkenyl, optionally substituted cycloalkyl, optionally substituted aralkyl, optionally substituted aryl or optionally substituted heterocyclyl, it being possible for the sulphinyl or sulphonyl radical to be in the α- to δ-position, and
$R_3$ represents H or alkyl, and can assume the α- or ε-position,
improve the growth, fat to lean meat ratio and the feed utilisation in animals.

It is known that for molecules with one centre of asymmetry there are two enantiomers, and for molecules with two centres of asymmetry there are two diastereomers and hence two enantiomer pairs.

The sulphinyl- or sulphonyl-azacycloheptan-2-ones according to the invention, of the formula (I), possess two centres of asymmetry or one centre of asymmetry, and accordingly it is intended that the present invention relates to all optical isomers and diastereomers.

Separation into these isomers can be effected by known methods.

The sulphinyl- and sulphonyl-azacycloheptan-2-ones according to the invention exhibit a surprisingly strongly pronounced nutritive effect which has not been found hitherto in compounds of this class of substance; in addition, they exhibit neither a mutagenic action (Ames test) nor an oestrogenic action, and hence represent an enrichment of the art.

Particularly preferred sulphinyl and sulphonyl-azacycloheptan-2-ones are those of the general formula (Ia)

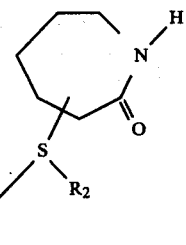

in which n and $R_2$ have the meaning given above, and the sulphinyl or sulphonyl radical is in the α- or β-position.

Furthermore, it has been found that the new sulphinyl- and sulphonyl-azacycloheptan-2-ones of the general formula (I) are obtained when
(a) thioethers of the formula (II)

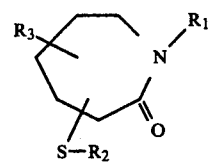

in which $R_1$, $R_2$ and $R_3$ have the meaning given above, and the sulphenyl radical is in the α- up to δ-position, are reacted with suitable oxidising agents, if appropriate in the presence of inert solvents.

(b) The 3-sulphonyl-azacycloheptan-2-ones according to the invention, of the formula (III)

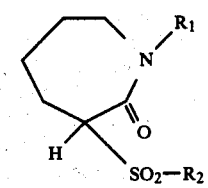

in which $R^1$ and $R^2$ have the meaning given above, can also be obtained by reacting 3-halogeno-azacycloheptan-2-ones of the formula (IV)

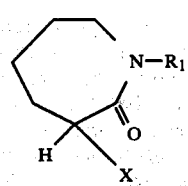

in which
$R^1$ has the meaning given above and
X represents halogen,
with sulphinates of the formula (V)

$$M^{\oplus}{}^{\ominus}O_2S-R_2 \qquad (V)$$

in which
$R_2$ has the meaning given above and
$M^{\oplus}$ represents an alkali metal cation, including $NR_4^{\oplus}$ wherein R represents H, $C_1$–$C_4$-alkyl, if appropriate in the presence of inert solvents.

Process a

If, for example, 3-(phenylthio)-azacycloheptan-2-one and m-chloroperbenzoic acid are used as starting materials, the course of the reaction can be represented by the following equation:

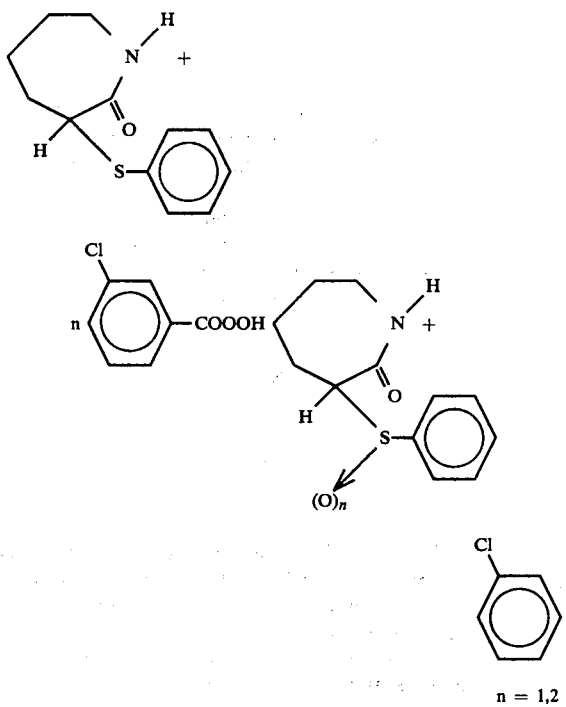

In the formula (I), optionally substituted alkyl $R_1$ and $R_3$ are straight-chain or branched alkyl radicals having up to 4 carbon atoms. Optionally substituted methyl, ethyl, n- and i-propyl, n-, i- and t-butyl may be mentioned as examples. Optionally substituted aryl $R_1$ represents optionally substituted phenyl, biphenyl or naphthyl, the substituents being in the o-, m- or p-position.

Optionally substituted acyl $R_1$ preferably denotes acetyl, propionyl and benzoyl.

Alkylcarbamoyl $R_1$ represents carbamoyl radicals having up to 4, in particular up to 2, carbon atoms in the alkyl part, and methyl- and ethylcarbamoyl may be mentioned as examples.

Optionally substituted alkyl $R_2$ represents straight-chain or branched alkyl having 1–18, preferably 1–12, carbon atoms. Optionally substituted methyl, ethyl, n- and i-propyl, n-, i- and t-butyl, pentyl, hexyl and dodecyl may be mentioned as examples.

Suitable optionally substituted alkenyl radicals $R_2$ are straight-chain or branched alkenyl radicals having up to 6, preferably up to 4, carbon atoms. The following may be mentioned as examples: ethenyl, propen-1-yl, propen-2-yl and buten-3-yl.

Optionally substituted cycloalkyl $R_2$ is monocyclic, bicyclic or tricyclic, and contains preferably 3 to 10, in particular 3 to 7, C atoms. Optionally substituted cyclopropyl, cyclobutyl, cyclopentyl, cyclohexyl, cyclohexenyl, cycloheptyl, bicyclo-[2,2,1]-heptyl and adamantyl may be mentioned as examples.

Optionally substituted aralkyl $R_2$ is aralkyl which is optionally substituted in the aryl part and/or alkyl part and has preferably 6 to 10, in particular 6, carbon atoms in the aryl part and preferably 1 to 4, in particular 1 or 2, carbon atoms in the alkyl part, it being possible for the alkyl part to be straight-chain or branched. Optionally substituted benzyl and phenylethyl may be mentioned as examples.

Optionally substituted aryl $R_2$ is aryl having preferably 6 to 10 carbon atoms in the aryl part. Optionally substituted phenyl or naphthyl may be mentioned as examples. Substituents in the phenyl ring are in the o-, m- or p-position.

Optionally substituted heterocyclyl radicals $R_2$ are heteroparaffinic, heteroaromatic or heteroolefinic 5-membered to 7-membered, preferably 5-membered or 6-membered, rings having preferably 1 to 3, in particular 1 or 2, identical or different hetero atoms. Hereto atoms are oxygen, sulphur or nitrogen. Optionally substituted thienyl, furyl, oxazolyl, isoxazolyl, thiazolyl, isothiazolyl, pyrrolyl, imidazolyl, pyrazolyl, oxadiazolyl, thiatriazolyl, tetrazolyl, pyridyl, pyrazinyl, pyrimidinyl, tetrahydrofuranyl, dioxanyl, pyrrolidinyl, piperidinyl and morpholinyl are examples of such moieties.

It is also possible for the heterocyclic rings to be fused to one or more radicals from the benzene series.

Optionally substituted alkyl, alkenyl, cycloalkyl, aralkyl, aryl and heterocyclyl radicals can carry one or more, preferably 1 to 3, in particular 1 or 2, identical or different radicals $R_4$, $R_4$ representing straight-chain or branched alkyl having preferably 1 to 6, in particular 1 to 4, C atoms, for example methyl, ethyl, n- and i-propyl, n-, i- and t-butyl, $CF_3$, $CCl_3$ and aryl, for example phenyl, lower alkyl-oxy-, preferably $CH_3O$— or $C_2H_5O$—, and aryl-oxy, for example phenoxy, and furthermore lower alkyl-thio, for example $CH_3S$— or $C_2H_5S$—, or HCO—NH—, di-(lower alkyl)-amino, for example dimethylamino or diethylamino, lower alkyl-O—CO—, for example $CH_3O$—CO— and $C_2H_5O$—CO—, halogen, preferably fluorine, chlorine or bromine, —C≡N, COOH, —$NH_2$ and $NO_2$.

Some of the thioethers of the formula (II) which are used according to the invention are known, or these compounds can be prepared by known processes (Faserforsch. u. Textiltechn. 14, 368–374 (1963), Aust. J. Chem. 34, 569–81 (1981)).

The oxidising agents which can be used according to the invention are likewise known, and hydrogen peroxide, performic acid, peracetic acid, perbenzoic acid, m-chloroperbenzoic acid, sodium metaperiodate and atmospheric oxygen may be mentioned as examples. Further suitable oxidising agents may be found in C Ferri, Reaktionen der organischen Synthese (Reactions of organic synthesis) G. Thieme Verlag, Stuttgart 1978, page 470).

Suitable diluents are all inert organic solvents. These preferably include chlorinated hydrocarbons, such as chlorinated alkanes, for example methylene chloride, chloroform, carbon tetrachloride, 1,2-dichloroethane, 1,2,2-trichloroethane; and halogenated benzene for example chlorobenzene; alcohols, especially $C_1$–$C_3$-alkanols, preferably methanol, ethanol and isopropanol; lower fatty acids, preferably formic acid, acetic acid and propionic acid, and water. The process according to the invention can be carried out exclusively in the presence of one or more organic solvents, or in the presence of water and one or more water-immiscible solvents.

The reaction temperatures can be varied within a relatively wide range. In general, the reaction is carried out at between about −20° C. and about +100° C., preferably between 0° C. and +60° C. The reaction can be carried out under atmospheric pressure as well as under reduced and elevated pressure. In general, the reaction is carried out under atmospheric pressure.

In carrying out the process according to the invention, the stoichiometric amount of oxidising agent in each case is employed for the preparation of the sulphoxides ((I), n=1) or the sulphones ((I), n=2).

Working up the reaction mixtures to isolate the compounds according to the invention is effected throughout in a generally known manner.

Process (b)

If, for example, α-bromo-caprolactam and sodium (4-chlorophenyl)-sulphinate are used as starting materials, the course of the reaction can be represented by the following equation:

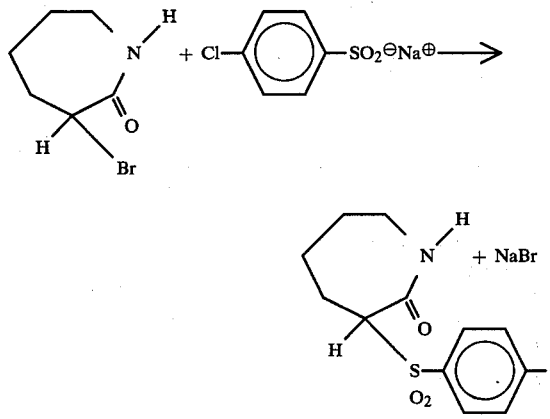

In the formula (IV),

X represents halogen, preferably chlorine, bromine and iodine, in particular chlorine and bromine.

R1 has the meaning given above.

α-Halogeno-caprolactams which can be used according to the invention are known, or can be prepared by known processes (for example, J. Amer. Chem. Soc. 80, 6238–6244 (1958)).

In the general formula (V),

R2 has the meaning given above, and

M⊕ represents an alkali metal cation or NR4+, wherein R represents H, C1–C4-alkyl, preferably the sodium or potassium cation including.

The alkali metal sulphinates which can be used according to the invention are known (Houben-Weyl, G. Thieme Verlag, Stuttgart, 1955, Vol. IX, pages 289–342).

Suitable diluents are all inert organic solvents. These preferably include alcohols, especially C1–C3-alkanols, such as methanol, ethanol and isopropanol; ethers such as dialkyl ethers, for example, dimethyl ether or diethyl ether, or cyclic ethers, such as dioxane or tetrahydrofuran, dipolar aprotic solvents such as dimethylsulphoxide, dimethylformamide and N-methylpyrrolidone, and water.

The process according to the invention can be carried out exclusively in the presence of one or more solvents or in the presence of water and one or more water-immiscible solvents.

The reaction temperatures can be varied within a relatively wide range. In general, the reaction is carried out at between about 0° C. and +250° C., preferably between +50° and +190° C. The reaction can be carried out under atmospheric pressure, and also under reduced and elevated pressure. In general the reaction is carried out under atmospheric pressure.

In carrying out the process according to the invention, the starting materials are employed in equimolar amounts, but it may be advantageous to use the alkali metal sulphinate of the general formula (V) in excess in order to increase the reaction velocity.

Working up the reaction mixtures to isolate the compounds according to the invention is effected throughout in a generally known manner.

The following are individual examples of the new active compounds all of which can be prepared by the processes outlined above or shown infra by working examples:

3-(butylsulphinyl)-azacycloheptan-2-one
4-(butylsulphinyl)-azacycloheptan-2-one
5-(butylsulphinyl)-azacycloheptan-2-one
6-(butylsulphinyl)-azacycloheptan-2-one
3-[(2-hydroxyethyl)-sulphinyl]-azacycloheptan-2-one
3-[(carboxy-methyl)-sulphinyl]-azacycloheptan-2-one
4-[(carboxy-methyl)-sulphinyl]-azacycloheptan-2-one
5-[(carboxy-methyl)-sulphinyl]-azacycloheptan-2-one
6-[(carboxy-methyl)-sulphinyl]-azacycloheptan-2-one
3-[(2-carboxy-2-amino-ethyl)-sulphinyl]-azacycloheptan-2-one
4-[(2-carboxy-2-amino-ethyl)-sulphinyl]-azacycloheptan-2-one
5-[(2-carboxy-2-amino-ethyl)-sulphinyl]-azacycloheptan-2-one
6-[(2-carboxy-2-amino-ethyl)-sulphinyl]-azacycloheptan-2-one
3-(dodecylsulphinyl)-azacycloheptan-2-one
3-(cyclohexylsulphinyl)-azacycloheptan-2-one
4-(cyclopentylsulphinyl)-azacycloheptan-2-one
3-(benzylsulphinyl)-azacycloheptan-2-one
4-(benzylsulphinyl)-azacycloheptan-2-one
5-(benzylsulphinyl)-azacycloheptan-2-one
6-(benzylsulphinyl)-azacycloheptan-2-one
3-(allylsulphinyl)-azacycloheptan-2-one
4-(allylsulphinyl)-azacycloheptan-2-one
5-(allylsulphinyl)-azacycloheptan-2-one
6-(allylsulphinyl)-azacycloheptan-2-one
3-[(3-chloro-prop-2-enyl)sulphinyl]-azacycloheptan-2-one
4-[(3-chloro-prop-2-enyl)sulphinyl]-azacycloheptan-2-one
3-[(3,3-dichloro-prop-2-enyl)sulphinyl]-azacycloheptan-2-one
3-(phenylsulphinyl)-azacycloheptan-2-one
4-(phenylsulphinyl)-azacycloheptan-2-one
3-[(4-chlorophenyl)sulphinyl]-azacycloheptan-2-one
4-[(4-chlorophenyl)sulphinyl]-azacycloheptan-2-one
5-[(4-chlorophenyl)sulphinyl]-azacycloheptan-2-one
6-[(4-chlorophenyl)sulphinyl]-azacycloheptan-2-one
3-[(3-chlorophenyl)sulphinyl]-azacycloheptan-2-one
4-[(3-chlorophenyl)sulphinyl]-azacycloheptan-2-one
5-[(3-chlorophenyl)sulphinyl]-azacycloheptan-2-one
6-[(3-chlorophenyl)sulphinyl]-azacycloheptan-2-one
3-[(2-chlorophenyl)sulphinyl]-azacycloheptan-2-one
4-[(2-chlorophenyl)sulphinyl]-azacycloheptan-2-one
5-[(2-chlorophenyl)sulphinyl]-azacycloheptan-2-one
6-[(2-chlorophenyl)sulphinyl]-azacycloheptan-2-one
3-[(3,4-dichlorophenyl)sulphinyl]-azacycloheptan-2-one
4-[(3,4-dichlorophenyl)sulphinyl]-azacycloheptan-2-one
3-[(2,4-dichlorophenyl)sulphinyl]-azacycloheptan-2-one
4-[(2,4-dichlorophenyl)sulphinyl]-azacycloheptan-2-one
3-[(3,5-dichlorophenyl)sulphinyl]-azacycloheptan-2-one
4-[(3,5-dichlorophenyl)sulphinyl]-azacycloheptan-2-one
3-[(3-fluoro-4-chloro-phenyl)sulphinyl]-azacycloheptan-2-one
4-[(3-fluoro-4-chloro-phenyl)sulphinyl]-azacycloheptan-2-one
3-[(3-trifluoromethyl-phenyl)sulphinyl]-azacycloheptan-2-one
4-[(3-trifluoromethyl-phenyl)sulphinyl]-azacycloheptan-2-one
3-[(4-methylphenyl)sulphinyl]-azacycloheptan-2-one
4-[(4-methylphenyl)sulphinyl]-azacycloheptan-2-one
3-[(4-nitrophenyl)sulphinyl]-azacycloheptan-2-one
4-[(4-nitrophenyl)sulphinyl]-azacycloheptan-2-one
3-[(4-bromophenyl)sulphinyl]-azacycloheptan-2-one
4-[(4-bromophenyl)sulphinyl]-azacycloheptan-2-one
3-[(4-aminophenyl)sulphinyl]-azacycloheptan-2-one
4-[(4-aminophenyl)sulphinyl]-azacycloheptan-2-one
3-[(2-carboxyphenyl)sulphinyl]-azacycloheptan-2-one
4-[(2-carboxyphenyl)sulphinyl]-azacycloheptan-2-one
3-[(4-cyanophenyl)sulphinyl]-azacycloheptan-2-one -continued 4-[(4-cyanophenyl)sulphinyl]-azacycloheptan-2-one
3-[(3-ethoxy-4-chloro-phenyl)sulphinyl]-azacycloheptan-2-one
4-[(3-ethoxy-4-chloro-phenyl)sulphinyl]-azacycloheptan-2-one
3-[(4-dimethylaminophenyl)sulphinyl]-azacycloheptan-2-one
1-methyl-3-allylsulphinyl-azacycloheptan-2-one
1-acetyl-3-allylsulphinyl-azacycloheptan-2-one
1-methylcarbamoyl-3-allylsulphinyl-azacycloheptan-2-one
1-ethyl-3-[(4-chlorophenyl)sulphinyl]-azacycloheptan-2-one
1-phenyl-3-[(4-chlorophenyl)sulphinyl]-azacycloheptan-2-one
1-phenyl-4-[(4-chlorophenyl)sulphinyl9 -azacycloheptan-2-one
1-acetyl-3-[(4-chlorophenyl)sulphinyl]-azacycloheptan-2-one
1-acetyl-4-[(4-chlorophenyl)sulphinyl]-azacycloheptan-2-one
1-propionyl-3-[(4-chlorophenyl)sulphinyl]-azacycloheptan-2-one
1-propionyl-4-[(4-chlorophenyl)sulphinyl]-azacycloheptan-2-one
1-methylcarbamoyl-3-[(4-chlorophenyl)sulphinyl]-azacycloheptan-2-one
1-methylcarbamoyl-4-[(4-chlorophenyl)sulphinyl]-azacycloheptan-2-one
5-(tert.-butyl)-3-[(4-chlorophenyl)sulphinyl]-azacycloheptan-2-one
3-(butylsulphonyl)-azacycloheptan-2-one
5-(butylsulphonyl)-azacycloheptan-2-one
3-(allylsulphonyl)-azacycloheptan-2-one
3-(benzylsulphonyl)-azacycloheptan-2-one
3-(phenylsulphonyl)-azacycloheptan-2-one
4-(phenylsulphonyl)-azacycloheptan-2-one
6-(phenylsulphonyl)-azacycloheptan-2-one
3-[(4-chlorophenyl)sulphonyl]-azacycloheptan-2-one
4-[(4-chlorophenyl)sulphonyl]-azacycloheptan-2-one
5-[(4-chlorophenyl)sulphonyl]-azacycloheptan-2-one
6-[(4-chlorophenyl)sulphonyl]-azacycloheptan-2-one
3-[(3-chlorophenyl)sulphonyl]-azacycloheptan-2-one
4-[(3-chlorophenyl)sulphonyl]-azacycloheptan-2-one
5-[(3-chlorophenyl)sulphonyl]-azacycloheptan-2-one
6-[(3-chlorophenyl)sulphonyl]-azacycloheptan-2-one
3-[(2-chlorophenyl)sulphonyl]-azacycloheptan-2-one
4-[(2-chlorophenyl)sulphonyl]-azacycloheptan-2-one
5-[(2-chlorophenyl)sulphonyl]-azacycloheptan-2-one
6-[(2-chlorophenyl)sulphonyl]-azacycloheptan-2-one
3-[(2,4-dichlorophenyl)sulphonyl]-azacycloheptan-2-one
4-[(2,4-dichlorophenyl)sulphonyl]-azacycloheptan-2-one
3-[(3,4-dichlorophenyl)sulphonyl]-azacycloheptan-2-one
4-[(3,4-dichlorophenyl)sulphonyl]-azacycloheptan-2-one
3-[(3,5-dichlorophenyl)sulphonyl]-azacycloheptan-2-one
4-[(3,5-dichlorophenyl)sulphonyl]-azacycloheptan-2-one
3-[(3-trifluoromethyl-phenyl)sulphonyl]-azacycloheptan-2-one
4-[(3-trifluoromethyl-phenyl)sulphonyl]-azacycloheptan-2-one
3-[(4-methylphenyl)sulphonyl]-azacycloheptan-2-one
4-[(4-methylphenyl)sulphonyl]-azacycloheptan-2-one
3-[(4-nitrophenyl)sulphonyl]-azacycloheptan-2-one
4-[(4-nitrophenyl)sulphonyl]-azacycloheptan-2-one
3-[(4-aminophenyl)sulphonyl]-azacycloheptan-2-one
4-[(4-aminophenyl)sulphonyl]-azacycloheptan-2-one
3-[(2-carboxyphenyl)sulphonyl]-azacycloheptan-2-one
4-[(2-carboxyphenyl)sulphonyl]-azacycloheptan-2-one
3-[(4-cyanophenyl)sulphonyl]-azacycloheptan-2-one
4-[(4-cyanophenyl)sulphonyl]-azacycloheptan-2-one
3-[(4-fluorophenyl)sulphonyl]-azacycloheptan-2-one
4-[(4-fluorophenyl)sulphonyl]-azacycloheptan-2-one
1-acetyl-3-[(4-chlorophenyl)sulphonyl]-azacycloheptan-2-one
1-acetyl-4-[(4-chlorophenyl)sulphonyl]-azacycloheptan-2-one
1-propionyl-3-[(4-chlorophenyl)sulphonyl]-azacycloheptan-2-one
1-propionyl-4-[(4-chlorophenyl)sulphonyl]-azacycloheptan-2-one
1-methylcarbamoyl-3-[(4-chlorophenyl)sulphonyl]-azacycloheptan-2-one
1-methylcarbamoyl-4-[(4-chlorophenyl)sulphonyl]-azacycloheptan-2-one
1-ethyl-3-[(3,4-dichlorophenyl)sulphonyl]-azacycloheptan-2-one
1-ethyl-4-[(3,4-dichlorophenyl)sulphonyl]-azacycloheptan-2-one
1-acetyl-3-[(3,4-dichlorophenyl)sulphonyl]-azacycloheptan-2-one
1-acetyl-4-[(3,4-dichlorophenyl)sulphonyl]-azacycloheptan-2-one
1-propionyl-3-[(3,4-dichlorophenyl)sulphonyl]-azacycloheptan-2-one
1-propionyl-4-[(3,4-dichlorophenyl)sulphonyl]-azacycloheptan-2-one
3-[(benzothiazol-2-yl)sulphinyl]-azacycloheptan-2-one
4-[(benzothiazol-2-yl)sulphinyl]-azacycloheptan-2-one
3-[(benzothiazol-2-yl)sulphonyl]-azacycloheptan-2-one
4-[(benzothiazol-2-yl)sulphonyl]-azacycloheptan-2-one
3-[(pyrid-2-yl)sulphinyl]-azacycloheptan-2-one
4-[(pyrid-2-yl)sulphinyl]-azacycloheptan-2-one
3-[(pyrid-2-yl)sulphonyl]-azacycloheptan-2-one
4-[(pyrid-2-yl)sulphonyl]-azacycloheptan-2-one
3-[(2-(3-chloro-tetrahydrofuranyl))sulphinyl]9 -azacycloheptan-2-one
3-[(2-(3-chloro-tetrahydrofuranyl))sulphonyl]-azacycloheptan-2-one
3-[(2-(3-chloro-quinoxalinyl))sulphinyl]-azacycloheptan-2-one
3-[(2-(3-chloro-quinoxalinyl))sulphonyl]-azacycloheptan-2-one
3-[(1,2,4-triazol-3-yl)sulphinyl]-azacycloheptan-2-one
3-[(1,2,4-triazol-3-yl)sulphonyl]-azacycloheptan-2-one Surprisingly, the azacycloheptan-2-ones of the formula (I) according to the invention have the property of promoting and accelerating growth in animals and to improve the fat to lean meat ratio, so that these compounds can be used, for the purposes mentioned, in all areas of animal breeding and animal husbandry.

The activity of the compounds used according to the invention is largely independent of the species and sex of the animals. The azacycloheptan-2-ones of the formula (I) according to the invention prove particularly valuable in the rearing and keeping of young animals and fattening animals. The following stock animals and pets may be mentioned as examples of animals for which the compound can be used for promoting and accelerating growth: warm-blooded animals, such as cattle, pigs, horses, sheep, goats, cats, dogs, rabbits, fur-bearing animals, for example mink and chinchillas, poultry, for example chicken, geese, ducks, turkeys and broilers, pigeons, parrots and canaries, and cold-blooded animals, such as fish, for example carp, and reptiles, for example snakes.

Azacycloheptan-2-ones of the formula (I) are preferably used in the rearing and keeping of ruminants, such as calves, goats and sheep, and for pigs and chicks.

The amount of azacycloheptan-2-ones of the formula (I) which is administered to the animals to achieve the desired effect can be varied substantially. It is preferably about 0.5 to 500, in particular 1 to 100 mg/kg of body weight daily. The period of administration can vary and administration can be effected so long as beneficial results are observed. The appropriate amount of active compound and the appropriate period of administration are indicated above but may further vary depending, in particular, on the species, age, sex, state of health and nature of keeping of the animals, and any changes which should desirably be effected can easily be determined by any expert.

The compounds are administered to the animals by the customary methods. The nature of the administration depends, in particular, on the species, the behaviour and the state of health of the animals. Thus, administration can be effected orally or parenterally, once or several times daily at regular or irregular intervals. For reasons of expediency, in most cases oral administration, in particular in the rhythm of the intake of food and/or drink by the animals, is to be preferred.

The compounds can be administered as pure substances or in the formulated form, that is to say mixed with non-toxic inert verterinary carriers; by these there are to be understood solid, semi-solid or liquid diluents, fillers and formulation auxiliaries of all kinds.

Azacycloheptan-2-ones of the formula (I), optionally in the formulated form, can also be administered in a suitable form together with pharmaceutical active compounds, mineral salts, trace elements, vitamins, proteins, fats, colorants, and/or flavouring agents.

Oral administration together with the feed and/or drinking water is recommended, the active compounds being added to the total amount or only portions of the feed and/or drinking water, as required.

The compounds can be admixed to the feed and/or drinking water in accordance with customary methods by simple mixing as pure substances, preferably in the finely divided form or in the formulated form mixed with edible non-toxic carriers, and optionally also in the form of a premix or a feed concentrate.

The feed and/or drinking water can contain the active compound according to the invention in a concentration of, for example, about 5 to 500 ppm, in particular 5 to 100 ppm. The optimum level of the concentration of the active compound in the feed and/or drinking water depends, in particular, on the amount of feed and/or drinking water taken by the animals, and can easily be determined by any person reasonably skilled in the art.

The nature of the feed and its composition is irrelevant. All the customary, commercially available or specific feed compositions, which preferably contain the customary equilibrium of energy substances and builder substances, including vitamins and mineral substances, necessary for balanced nutrition, can be used. The feed can be composed, for example, of vegetable substances, for example hay, beet, cereals and cereal by-products, animal substances, for example meat, fats and bone meal, fish products, vitamins, for example vitamin A, D complex and B complex, proteins, aminoacids, for example DL methionine, and inorganic substances, for example lime and sodium chloride.

Feed concentrates contain azacycloheptan-2-ones of the formula (I) alongside edible substances, for example rye flour, maize flour, soya bean flour or lime, optionally with further nutrients and builder substances, as well as proteins, mineral salts and vitamins. They can be prepared by the customary mixing methods.

In premixes and feed concentrations, preferably, the active compounds can optionally also be protected from air, light and/or moisture by suitable agents which coat its surface, for example with non-toxic waxes or gelatine.

The following is an example of the composition of a feed for rearing chicks, which contains azacycloheptan-2-ones of the formula (I): 200 g of wheat, 340 g of maize, 361 g of coarse soya bean meal, 60 g of beef tallow, 15 g of dicalcium phosphate, 10 g of calcium carbonate, 4 g of iodinated sodium chloride, 7.5 g of a vitamin/mineral mixture and 2.5 g of an active compound premix (as defined below) give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains azacycloheptan-2-ones of the formula (I) in the desired amount, for example 100 mg, and also 1 g of DL-methionine as well as an amount of soya bean flour such that 2.5 g of a premix are formed.

The following is an example of the composition of a feed for rearing pigs, which contains the active compound according to the invention: 630 g of shredded cereal feed (composed of 200 g of maize, 150 g of shredded barley, 150 g of shredded oats and 130 g of shredded wheat), 80 g of fish meal, 60 g of coarse soya bean meal, 60 g of tapioca meal, 38 g of egg yeast, 50 g of a vitamin/mineral mixture for pigs (composition, for example, as for the chick feed), 30 g of linseed cake meal, 30 g of maize gluten feed, 10 g of soya bean oil, 10 g of sugar cane molasses and 2 g of an active compound premix (composition, for example, as for the chick feed) give, after careful mixing, 1 kg of feed.

The feed mixtures indicated are intended preferably for rearing and fattening chicks or pigs respectively, but they can also be used, in the same or similar composition, for rearing and fattening other animals.

14-day feeding tests on chicks and 6-week feeding tests on broilers, which contained 5 ppm to 500 ppm of a compound of the formula (I) with the feed, showed a significant increase in weight in the animals treated with azacycloheptan-2-ones of the formula (I) in comparison with animals fed without the addition of azacycloheptan-2-ones of the formula (I).

EXAMPLE 1

Preparation of 3-[(4-chlorophenyl)thio]-azacycloheptan-2-one 54 g (1.0 mol) of sodium methylate and 144.6 g (1.0 mol) of 4-chlorothiophenol are initially introduced into 500 mL of methanol, and a methanolic solution of 192 g (1.0 mol) of α-bromocaprolactam is added dropwise at room temperature. After the exothermic reaction has ceased, the mixture is stirred for a further 3 hours at room temperature, the precipitated sodium bromide is then filtered off under suction and the mother liquor is evaporated down in vacuo. The precipitated crystals are filtered off under suction.

Yield: 250 g (=98% of theory).
M.p: 176° C.

EXAMPLE 2

Preparation of 5-(butylthio)-azacycloheptan-2-one 6.8 g (0.1 mol) of sodium ethylate and 9 g (0.1 mol) of butanethiol are initially introduced into 100 ml of ethanol, and 14.8 g (0.1 mol) of 5-chloro-azacycloheptan-2-one are added at room temperature. After the mixture has been boiled under reflux for 10 hours, the precipitated sodium chloride is filtered off under suction, the mother liquor is evaporated down in vacuo and the residue is distilled.

Yield: 10.5 g (=52% of theory).
B.p: 120° C./0.9 mbar.

EXAMPLE 3

Preparation of 1-(methylcarbamoyl)-3-[(4-chlorophenyl)thio]-azacycloheptan-2-one 25.6 g (0.1 mol) of 3-[(4-chlorophenyl)thio]-azacycloheptan-2-one together with 5.7 g (0.1 mol) of methyl isocyanate and 100 mg of dibutyl-tin dilaurate in 150 ml of absolute toluene are boiled under reflux for 5 hours. After the mixture has cooled, the solvent is stripped off in vacuo, and the oily residue is used for further reactions.

EXAMPLE 4

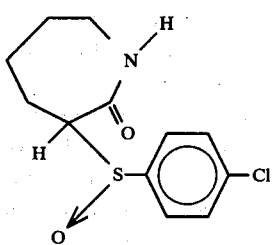

11 g of 30% strength hydrogen peroxide are added to a solution of 25.6 g (0.1 mol) of 3-[(4-chlorophenyl)thio]-azacycloheptan-2-one in 200 ml of glacial acetic acid, and the reaction mixture is allowed to stand for 48 hours at room temperature.

Thereafter, the glacial acetic acid is stripped off in vacuo, and the residue is recrystallised from methanol.

Yield: 21 g (=72% of theory).

M.p.: 185°–189° C. (methanol).

The following compounds were prepared analogously to that of Example 4:

| Example No. | Formula | Yield (%) | B.p. (°C./mbar) or m.p. (°C.) |
|---|---|---|---|
| 5 | 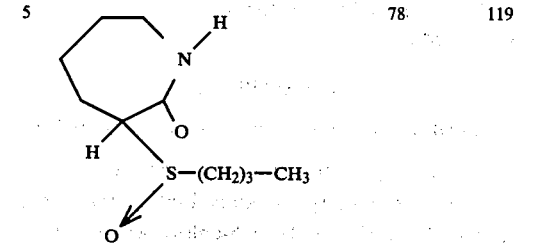 | 78 | 119 |
| 6 | 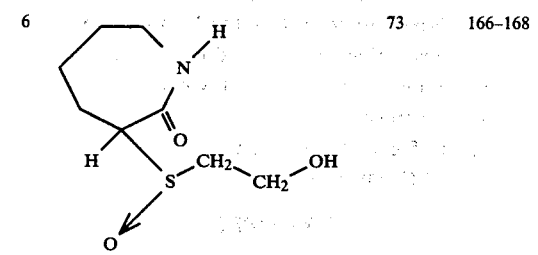 | 73 | 166–168 |
| 7 | 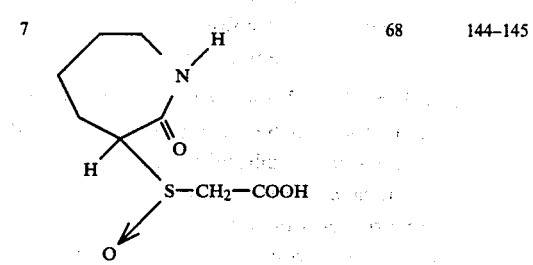 | 68 | 144–145 |
| 8 | 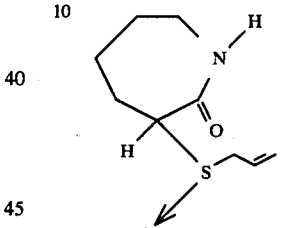 | 56 | 130–131 |
| 9 |  | 86 | 158–162 |

The following compounds were prepared analogously to that of Example 4:

| Example No. | Formula | Yield (%) | B.p. (°C./mbar) or m.p. (°C.) |
|---|---|---|---|
| 10 | 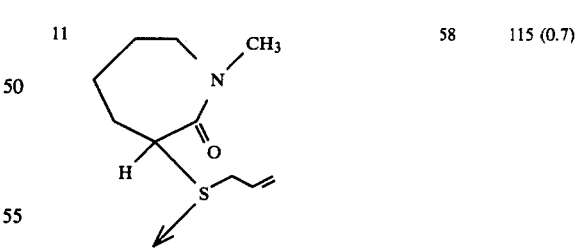 | 67 | 98–100 |
| 11 | 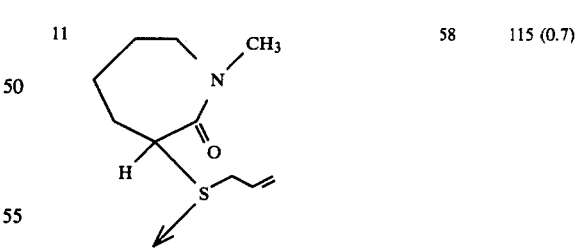 | 58 | 115 (0.7) |
| 12 | 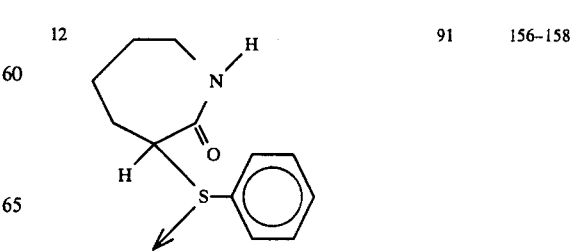 | 91 | 156–158 |

-continued

| Example No. | Formula | Yield (%) | B.p. (°C./mbar) or m.p. (°C.) |
|---|---|---|---|
| 13 | [structure: N-methyl azepanone with S(O)-C6H4-Cl] | 85 | 162–164 |
| 14 | [structure: azepanone with S(O)-C(=N)-S-benzothiazole] | 93 | 187–189 |
| 15 | [structure: C4H9-S(O)- azepanone] | 48 | 135 (0.9) |

The following compounds were prepared analogously to that of Example 4:

| Example No. | Formula | Yield (%) | B.p. (°C./mbar) or m.p. (°C.) |
|---|---|---|---|
| 16 | [structure: N-(CH2)2-CN azepanone with S(O)-C6H4-Cl] | 79 | 143–148 |
| 17 | [structure: azepanone with S(O)-C6H4-CH3] | 83 | 176–177 |
| 18 | [structure: azepanone with S(O)-2,5-dichlorophenyl] | 62 | 178–180 |
| 19 | [structure: azepanone with S(O)-3,4-dichlorophenyl] | 91 | 180–182 |
| 20 | [structure: azepanone with S(O)-3,5-dichlorophenyl] | 87 | 155–156 |
| 21 | [structure: azepanone with S(O)-3-CF3-phenyl] | 81 | 153–155 |

The following compounds were prepared analogously to that of Example 4:

| Example No. | Formula | Yield (%) | B.p. (°C./mbar) or m.p. (°C.) |
|---|---|---|---|
| 22 | [structure: azepanone with S(O)-4-NH2-phenyl] | 54 | 175–179 |

-continued

| Example No. | Formula | Yield (%) | B.p. (°C./mbar) or m.p. (°C.) |
|---|---|---|---|
| 23 | [azepan-2-one with S(=O)-C6H4-NO2 substituent] | 58 | 173–176 |
| 24 | [azepan-2-one with S(=O)-C6H4-Cl (ortho) substituent] | 63 | 179–180 |
| 25 | [azepan-2-one with S(=O)-C6H4-NH2 substituent] | 38 | 101–105 (Decomposition) |
| 26 | [N-propionyl azepan-2-one with S(=O)-C6H4-Cl substituent] | 47 | 158–159 |

The following compounds were prepared analogously to that of Example 4:

| Example No. | Formula | Yield (%) | B.p. (°C./mbar) or m.p. (°C.) |
|---|---|---|---|
| 27 | [N-benzoyl azepan-2-one with S(=O)-C6H4-Cl substituent] | 62 | 126–129 |

| Example No. | Formula | Yield (%) | B.p. (°C./mbar) or m.p. (°C.) |
|---|---|---|---|
| Example 28 | [azepan-2-one with S(=O)-C6H4-Cl (para) substituent] | | |

20 g of m-chloroperbenzoic acid (80–90% strength) are added in portions to 25.6 g (0.1 mol) of 3-[(4-chlorophenyl)thio]-azacycloheptan-2-one in 200 ml of chloroform at room temperature. After the exothermic reaction has ceased, the mixture is stirred for a further 14 hours at room temperature and then neutralised with sodium bicarbonate solution. The organic phase is separated off and evaporated down. The crystalline residue is recrystallised from methanol.
Yield: 24.5 g (=90% of theory).
M.p.: 189°–192° C.

The following compounds were prepared analogously to that of Example 28:

| Example 29 | | Yield (%) | M.p. (°) |
|---|---|---|---|
| | [azepan-2-one with S(=O)-pyridyl substituent] | 53 | 147–148 |

| Example No. | Formula | Yield (%) | B.p. (°C./mbar) or m.p. (°C.) |
|---|---|---|---|
| 30 | [N-(methylcarbamoyl) azepan-2-one with S(=O)-(CH2)3-CH3 substituent] | 59 | 120 |
| 31 | [N-(methylcarbamoyl) azepan-2-one with S(=O)-C12H25 substituent] | 47 | 59 |

| Example No. | Formula | Yield (%) | B.p. (°C/mbar) or m.p. (°C) |
|---|---|---|---|
| 32 | [azacycloheptanone with N-C(O)NHCH3 and S-CH2-CH=CH2, S→O] | 41 | 114 |
| 33 | [azacycloheptanone with N-C(O)NHCH3 and S-(4-chlorophenyl), S→O] | 52 | 132–136 |
| Example 34 | [azacycloheptan-2-one with S-(4-chlorophenyl), S→O] | | |

21.4 g (0.1 mol) of sodium metaperiodate are added to a solution of 25.6 g (0.1 mol) of 4-[(4-chlorophenyl)thio]-azacycloheptan-2-one in 100 ml of methanol, and the mixture is stirred for 100 hours at room temperature. Thereafter, the precipitate is filtered off under suction, the mother liquor is evaporated down and the residue is crystallised.

Yield: 18 g (=66% of theory).
M.p.: 136°–138° C.

The following compounds were prepared analogously to that of Example 34:

| Example No. | Formula | Yield (%) | B.p. (°C/mbar) or m.p. (°C) |
|---|---|---|---|
| 35 | [azacycloheptan-2-one with S-(4-methylphenyl), S→O] | 77 | 167–168 |
| 36 | [azacycloheptan-2-one with S-(4-nitrophenyl), S→O] | 53 | 138–140 |
| 36a | [azacycloheptan-2-one with S-(2-carbomethoxyphenyl), S→O] | 50 | melting point: 133–136 |
| Example 37 | [azacycloheptan-2-one with SO2-(4-chlorophenyl)] | | |

44 g of m-chloroperbenzoic acid (80–90% strength) are added in portions to 25.6 g (0.1 mol) of 3-[(4-chlorophenyl)thio]-azacycloheptan-2-one in 200 ml of chloroform, at room temperature. After the exothermic reaction has ceased, the mixture is stirred for a further 10 hours at room temperature and then neutralised with sodium bicarbonate solution. The organic phase is separated off and evaporated down. The crystalline residue is recrystallised from methanol.

Yield: 24 g (=83% of theory).
M.p.: 171° C.

The following compounds were prepared analogously to that of Example 37:

| Example No. | Formula | Yield (%) | B.p. (°C/mbar) or m.p. (°C) |
|---|---|---|---|
| 38 | [azacycloheptanone with N-C(O)NH-CH3 and SO2-C12H25] | 41 | 61 |

-continued

| Example No. | Formula | Yield (%) | B.p. (°C./mbar) or m.p. (°C.)₃ |
|---|---|---|---|
| 39 | 2,5-dichlorophenylsulfonyl caprolactam | 83 | 205–207 |
| 40 | 3-trifluoromethylphenylsulfonyl caprolactam | 73 | 174–176 |
| 41 | 4-nitrophenylsulfonyl caprolactam | 48 | 188–89 |
| 42 | 2-chlorophenylsulfonyl caprolactam | 67 | 162–163 |
| 43 | 3,4-dichlorophenylsulfonyl caprolactam | 86 | 227–229 |
| 44 | 3,5-dichlorophenylsulfonyl caprolactam | 79 | 194–196 |
| 45 | N-propionyl-(4-chlorophenylsulfonyl) caprolactam | 48 | 141–142 |
| 46 | N-benzoyl-(4-chlorophenylsulfonyl) caprolactam | 67 | 154–155 |
| 47 | 4-methylphenylsulfonyl caprolactam (α,β labeled) | 53 | 194–195 |
| 48 | 4-chlorophenylsulfonyl caprolactam | 68 | 140–142 |
| 48a | 2-carbomethoxyphenylsulfonyl caprolactam (α,β labeled) | 83 | 184–186 |
| Example 49 | phenylsulfonyl caprolactam | 83 | 184–186 |

192 g of α-bromocaprolactam and 164 g of Na benzenesulphinate in 600 ml of dimethylformamide are boiled reflux for 10 hours. Thereafter, the precipitated salt is filtered off under suction, and the mother liquor is evaporated down in vacuo. The precipitated crystals are recrystallised from acetone.

Yield: 119 g (32 47% of theory).
M.p.: 180°–181° C.

The following compounds were prepared analogously to that of Example 49:

| Example No. | Formula | Yield (%) | B.p. (°C./mbar) or m.p. (°C.) |
|---|---|---|---|
| 50 | | 66 | 175 |
| 51 | | 95 | 171 |

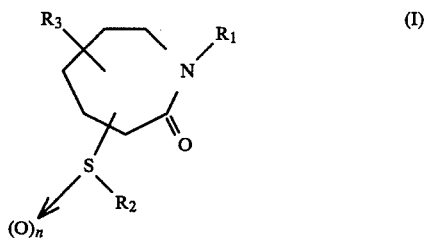

We claim:

1. A sulphinyl- or sulphonyl-azacycloheptan-2-one of the formula (I)

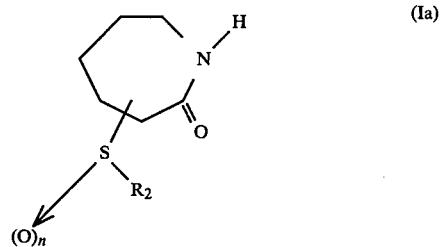

in which
n denotes 1 or 2,
$R^1$ represents H,
$C_1$–$C_4$-alkyl, optionally substituted by CN; CO(C$_1$–C$_4$-alkyl); benzoyl or $C_1$–$C_4$-carbamoyl,
$R^2$ denotes $C_1$–$C_{12}$-alkyl optionally substituted by $NH_2$, OH, COOH or phenyl; $C_2$–$C_4$-alkenyl; phenyl, optionally substituted by halogen, $C_1$–$C_4$-alkyl, $CF_3$, $NH_2$, $NO_2$, COO($C_1$–$C_4$-alkyl), pyridyl or benzothiazolyl, the sulphinyl or sulphonyl radical being in the α- to δ-position, and
$R_3$ represents H or $C_1$–$C_4$-alkyl, and is in the α-to ω-position.

2. A sulphinyl- or sulphonyl-azacycloheptan-2-one according to claim 1, of the formula (Ia)

(Ia)

in which n and $R_2$ have the meaning given in claim 1 and the sulphinyl or sulphonyl radical is in the α- or β-position.

3. A compound of claim 1 which is 3-[(4-chlorophenyl)-sulfinyl]-azacycloheptan-2-one.

4. A compound of claim 1 which is 4-[(4-chlorophenyl)-sulfinyl]-azacycloheptan-2-one.

5. A compound of claim 1 which is 4-[(4-methylphenyl)-sulfinyl]-azacycloheptan-2-one.

6. A compound of claim 1 which is 4-[(4-methylphenyl)-sulphonyl]-azacycloheptan-2-one.

7. A compound of claim 1 which is 3-[(4-chlorophenyl)-sulphonyl]-azacycloheptan-2-one.

8. A compound of claim 1 which is 4-[(4-chlorophenyl)-sulphonyl]-azacycloheptan-2-one.

9. A feed additive comprising a growth promoting amount of a sulphinyl- or sulphonyl-azacycloheptan-2-one of the formula (I) in claim 1 together with a veterinary feed.

10. A premix for the production of an animal feed, comprising a growth promoting amount of a sulphinyl- and sulphonyl-azacycloheptan-2-one of the formula (I) in claim 1 together with an inert veterinary carrier.

11. A method of promoting growth, improving fat to lean meat ratio in animals which comprises administering to a said animal a growth promoting, fat to lean meat ratio improving and feed utilizing amount of compound of claim 1.

* * * * *